United States Patent [19]
Chin

[11] Patent Number: 5,501,653
[45] Date of Patent: Mar. 26, 1996

[54] ABDOMINAL WALL LIFTING RETRACTOR WITH HINGED CROSS-MEMBER

[75] Inventor: Albert K. Chin, Palo Alto, Calif.

[73] Assignee: Origin Medsystems, Inc., Menlo Park, Calif.

[21] Appl. No.: 163,275

[22] Filed: Dec. 6, 1993

Related U.S. Application Data

[63] Continuation-in-part of Ser. No. 890,033, May 28, 1992, abandoned, Ser. No. 62,707, May 18, 1993, and Ser. No. 128,477, Sep. 28, 1993, abandoned, which is a continuation-in-part of Ser. No. 890,033, and Ser. No. 62,707, which is a continuation of Ser. No. 706,781, May 29, 1991, abandoned, said Ser. No. 890,033, is a continuation-in-part of Ser. No. 706,781.

[51] Int. Cl.$^6$ ..................................................... A61B 17/02
[52] U.S. Cl. ........................... 600/204; 600/216; 606/198
[58] Field of Search .............................. 128/20; 606/198, 606/191; 600/204, 215, 216

[56] References Cited

U.S. PATENT DOCUMENTS 1,060,350  4/1913  Miller .
1,275,520  8/1918  Bell .
1,618,261  2/1927  Arbogast .

(List continued on next page.)

FOREIGN PATENT DOCUMENTS 516114   5/1981  Australia ...................... A61B 10/00
0010650  5/1980  European Pat. Off. ....... A61M 31/00

(List continued on next page.)

OTHER PUBLICATIONS

G. Keen MS, FRCS, (ed.) "Operative Surgery & Management," pp. 334–335, (2nd. ed., Wright, Bristol, 1987).

R. F. Rintoul (ed.), "Farquharson's Textbook of Operative Surgery," pp. 286–289, (7th ed., Churchill Livingstone, New York, 1986).

ed. G. Berci, Endoscopy, Appleton–Century–Crofts, 1976, pp. 382–385 and 412.

Unknown—Laparoscopy for Sterilization, Section 1, A Chronology of Laparoscopy.

"New Surgical Procedures for Indirect Hernias"—Product leaflet for Herniastat™ disposable automatic surgical stapling device published by Innovative Surgical Devices, Inc., date unknown.

"A Tiny TV Camera is Fast Transforming Gallbladder Surgery," Wall Street Journal, Dec. 10, 1990, p. A1, continued on page A5.

A Comprehensive Guide to Purchasing [Hospital Supplies], V. Mueller & Co, Chicago, 1956, p. 829.

H. Nagai et al., "A New Method of Laparoscopic Cholecystectomy: An Abdominal Wall Lifting Technique without Penumoperitoneum," Surgical Laparoscopy and Endoscopy, vol. 1, No. 2, 1991, p. 126.

M. M. Gazayerli, "The Gazayerli Endoscopic Retractor Model 1," Surgical Laparoscopy and Endoscopy, vol. 1, No. 2, 1991, pp. 98–100.

Geza J. Jako & Stephen Rozsos, "Preliminary Report: Endoscopic Laser Microsurgical Removal of Human Gallbladder," J. Laparoendoscopic Surgery, vol. 1, No. 4, 1991.

*Primary Examiner*—Michael H. Thaler
*Attorney, Agent, or Firm*—Limbach & Limbach

[57] ABSTRACT

A method and apparatus for creating a surgical work space by lifting the abdominal wall and retracting abdominal organs during surgery utilizes a pair of lifting rods each hinged at their distal ends to opposite ends of an elongate cross-member. One of the lifting rods is slidable within a strap fastened to the proximal end of the other of the rods. The hinged relation of the lifting rods to the cross members and the sliding relation of the lifting rods to each other allow the apparatus to be pivoted into a streamlined configuration to facilitate insertion into a puncture opening in an abdominal cavity, and then to be pivoted into a triangular frame for defining an area of the abdominal wall to be lifted. After insertion the apparatus is locked into the triangular configuration, connected to a lifting arm, and lifted to cause the retraction rods to lift and support the abdominal wall.

9 Claims, 5 Drawing Sheets

U.S. PATENT DOCUMENTS

| | | | |
|---|---|---|---|
| 1,947,649 | 2/1934 | Kadavy | 128/20 |
| 2,663,020 | 12/1953 | Cushman | 128/303 |
| 2,841,148 | 7/1958 | Kadavy | 128/303 |
| 3,039,468 | 6/1962 | Price | 128/347 |
| 3,460,539 | 8/1969 | Anhalt, Sr. | 128/303.17 |
| 3,626,949 | 12/1971 | Shute | 128/344 |
| 3,717,151 | 2/1973 | Collett | 128/347 |
| 3,774,596 | 11/1973 | Cook | 128/5 |
| 3,782,370 | 1/1974 | McDonald | 128/20 |
| 3,831,587 | 8/1974 | Boyd | 128/6 |
| 3,863,639 | 2/1975 | Kleaveland | 128/303 R |
| 3,961,632 | 6/1976 | Moossun | 128/347 |
| 4,052,980 | 10/1977 | Grams et al. | 128/18 |
| 4,077,412 | 3/1978 | Moossun | 128/347 |
| 4,083,369 | 4/1978 | Sinnreich | 128/276 |
| 4,183,102 | 1/1980 | Guiset | 604/101 X |
| 4,240,433 | 12/1980 | Bordow | 128/347 |
| 4,254,762 | 3/1981 | Yoon | 128/4 |
| 4,291,687 | 9/1981 | Sinnreich | 128/129 |
| 4,357,940 | 11/1982 | Muller | 128/303 R |
| 4,430,076 | 2/1984 | Harris | 605/96 |
| 4,447,227 | 5/1984 | Kotsanis | 604/95 |
| 4,459,978 | 7/1984 | Kotsanis | 128/20 |
| 4,535,773 | 8/1985 | Yoon | 604/51 |
| 4,598,699 | 7/1986 | Garren et al. | 128/4 |
| 4,601,710 | 7/1986 | Moll | 604/165 |
| 4,654,030 | 3/1987 | Moll et al. | 604/165 |
| 4,662,955 | 5/1987 | Dries et al. | |
| 4,693,243 | 9/1987 | Buras | 128/207.25 |
| 4,705,040 | 11/1987 | Mueller et al. | 128/334 R |
| 4,709,697 | 12/1987 | Muller | 128/303 R |
| 4,744,363 | 5/1988 | Hasson | 128/331 |
| 4,763,635 | 8/1988 | Ballhause et al. | |
| 4,765,331 | 8/1988 | Petruzzi et al. | 128/303.14 |
| 4,775,371 | 10/1988 | Mueller, Jr. | 604/280 |
| 4,779,611 | 10/1988 | Grooters et al. | 128/4 |
| 4,919,152 | 4/1990 | Ger | 128/898 |
| 4,944,443 | 7/1990 | Oddsen et al. | 227/19 |
| 4,966,583 | 10/1990 | Debbas | 604/98 |
| 4,984,564 | 1/1991 | Yuen | 128/20 |
| 5,002,557 | 3/1991 | Hasson | 606/191 |
| 5,007,898 | 4/1991 | Rosenbluth et al. | 604/54 |
| 5,062,847 | 11/1991 | Barnes | 606/194 |
| 5,082,005 | 1/1992 | Kaldany | 128/850 |
| 5,083,576 | 1/1992 | Ruiz-Razura et al. | 128/898 |
| 5,100,426 | 3/1992 | Nixon | 606/170 |
| 5,122,122 | 6/1992 | Allgood | 604/174 X |
| 5,122,155 | 6/1992 | Ederbach | 606/213 |
| 5,141,515 | 8/1992 | Ederbach | 128/887 |
| 5,152,279 | 10/1992 | Wilk | 128/20 |
| 5,163,949 | 11/1992 | Bonutti | 606/198 X |
| 5,176,128 | 1/1993 | Andrese | 128/20 |
| 5,176,692 | 1/1993 | Wilk et al. | 606/151 |
| 5,176,697 | 1/1993 | Hasson et al. | 606/191 |
| 5,178,133 | 1/1993 | Pena | 128/20 |
| 5,188,630 | 2/1993 | Christaudias | 606/191 |
| 5,195,505 | 3/1993 | Josefsen | 128/20 |
| 5,195,507 | 3/1993 | Bilweis | 604/97 |
| 5,235,966 | 8/1993 | Jammer | 128/20 |
| 5,280,782 | 1/1994 | Wilk | 128/20 |
| 5,293,863 | 3/1994 | Zhu et al. | 128/20 |
| 5,318,012 | 6/1994 | Wilk | 128/20 |
| 5,318,013 | 6/1994 | Wilk | 128/20 |
| 5,339,801 | 8/1994 | Poloyko et al. | 128/20 |
| 5,351,679 | 10/1994 | Mayzels et al. | 128/20 |
| 5,403,343 | 4/1995 | Sugarbaker | 606/207 |

FOREIGN PATENT DOCUMENTS

| | | | |
|---|---|---|---|
| 0246086 | 11/1987 | European Pat. Off. | A61B 17/02 |
| 0251976 | 1/1988 | European Pat. Off. | A61M 29/02 |
| 0275230 | 7/1988 | European Pat. Off. | A61M 25/00 |
| 464463 | 1/1992 | European Pat. Off. | 606/198 |
| 2474304 | 7/1981 | France | A61B 17/00 |
| 2646088 | 10/1990 | France | A61M 29/04 |
| 2688695 | 5/1992 | France | A61B 17/00 |
| 1516411 | 7/1969 | Germany | |
| 2847633 | 5/1979 | Germany | |
| 8516286 | 9/1985 | Germany | A61B 17/02 |
| 9104383 | 7/1991 | Germany | A61B 17/02 |
| 736949 | 5/1980 | U.S.S.R. | A61B 1/00 |
| 797668 | 1/1981 | U.S.S.R. | A61B 17/02 |
| 1367947 | 1/1988 | U.S.S.R. | A61B 17/02 |
| 1577769 | 7/1990 | U.S.S.R. | A61B 17/02 |
| 2071502 | 9/1981 | United Kingdom | A61B 17/02 |
| WO9102493 | 3/1991 | WIPO | A61B 17/22 |
| WO91/14392 | 10/1991 | WIPO | A61B 1/32 |

ABDOMINAL WALL LIFTING RETRACTOR WITH HINGED CROSS-MEMBER

This application is a Continuation-in-Part of application Ser. No. 07/890,033, filed May 28, 1992 abanoned now, which is a Continuation-in-Part of application Ser. No. 07/706,781, filed May 29, 1991, now abandoned. This application is also a Continuation-In-Part of application Ser. No. 08/062,707, filed May 18, 1993, now abandoned, which is a Continuation of application Ser. No. 07/706,781, filed May 29, 1991, now abandoned. This application is also a Continuation-In-Part of application Ser. No. 08/128,477, filed Sep. 28, 1993, abandoned which is a Continuation-in-Part of application Ser. Nos. 07/890,033 and 08/062,707.

1. Field of the Invention

The present invention relates to the field of surgical retractors and particularly to lifting the abdominal wall and retracting the abdominal contents during laparoscopic surgery.

2. Background of the Invention

Laparoscopy dates back to the turn of the 20th Century. Early laparoscopic techniques were used primarily for diagnostic purposes to view the internal organs, without the necessity of conventional surgery. Since the 1930s, laparoscopy has been used for sterilization and, more recently, for suturing hernias. U.S. Pat. Nos. 4,919,152 and 4,944,443 are concerned with techniques for suturing hernias. Another recent innovation is the use of laparoscopic surgery for removing the gallbladder.

In the course of performing laparoscopic procedures in the abdomen, it is necessary to raise the abdominal wall to create space in which to work. A well-known method of raising the abdominal wall is to insufflate the abdominal cavity with a suitable insufflation gas, such as air, or carbon dioxide. A significant disadvantage of gas insufflation is that instruments must be passed into the abdominal cavity through gas-tight seals, which significantly reduce the surgeon's feel of the instruments.

Several mechanical alternatives to gas insufflation have been proposed. The Gazayerli Endoscopic Retractor Model 1, described in *SURGICAL LAPAROSCOPY AND ENDOSCOPY*, Vol. 1, No. 2, 1991, pages 98–100, has a rigid rod with a hinged blade at the distal end. The blade can rotate through 360 degrees about an axis perpendicular to the long axis of the rod. The blade is aligned with the long axis of the rod for insertion into the abdomen through a small puncture. Once inside the abdomen, the blade is swivelled through about 90 degrees to form a T-shaped structure. The proximal end of the rod can be raised by hand or by a rope, pulley and weight arrangement. Raising the rod causes the blade to engage the abdominal wall and to lift it.

French patent application no. 90-03980 shows a wire structure that is threaded into the abdomen through a small puncture to engage and to lift the abdominal wall. The application also shows a fan retractor that has a first angle-shaped member having a first leg that engages with the abdominal wall, a tubular second leg having a bore, and a third leg, remote from the first leg, that has a hook-shaped member on its end distal from the second leg. A second angle-shaped member has a first leg that engages with the abdominal wall, a second leg that pivots within the bore of the second leg of the first angle-shaped member, and a third leg, remote from the first leg, that serves as an operating lever for the second angle-shaped member. The first legs of the angle-shaped members are closed together to insert them into the abdominal cavity through an incision. The third leg of the second angle-shaped member is then operated to spread the first leg of the second angle-shaped member apart from the first leg of the first angle-shaped member. The first legs are engaged with the peritoneum inside the abdominal cavity. A lifting force is then applied to the hook-shaped member to lift the retractor and hence to lift the abdominal wall.

U.S. patent application Ser. Nos. 07/890,033, 08/062,707 and 08/128,477, the application of which this application is a Continuation-in-Part, and which are hereby incorporated by reference, describe a number of different mechanical devices that are inserted through one or more punctures into the abdomen. All or part of the device is then lifted to lift the abdominal wall away from the underlying abdominal organs. Some of the devices described in these applications utilize a fan retractor that is inserted in a closed condition into the abdomen, spread apart using pivoting movement once inside the abdomen, and brought into contact with the peritoneum inside the abdomen. The fan retractor is then raised by a lifting arm to lift the abdominal wall.

During lifting, loading forces are exerted by the abdominal wall on the legs of a fan retractor which may be great enough to cause downward deflection of the legs and also deflection of the legs towards each other. While slight deflection is necessary to prevent trauma of the tissue underlying the retractor legs, excessive downward deflection and inward collapse of the retractor legs can significantly decrease the size of the working space provided by retraction.

The working space provided by a fan retractor may also be obstructed in instances where a portion of the peritoneal tissue lining the abdominal wall drapes downwards into the cavity created by lifting. Currently available fan retractors are sometimes incapable of preventing this problem because the legs of the fan retractor do not prevent the draping tissue from caving between them. Draping abdominal tissue may also interfere with proper deployment of a fan retractor because the pivoting legs may catch on tissue located in their paths and thus necessitate removal and re-placement of the retractor.

OBJECTS AND SUMMARY OF THE INVENTION

It is an object of the present invention to provide an apparatus and method for mechanically retracting the abdominal wall to provide visualization of a portion of the abdominal cavity and working space within it. It is also an object of the present invention to provide a fan retractor capable of substantially resisting lateral forces imposed on the retractor legs by the abdominal wall during lifting so as to prevent the retractor legs from collapsing towards each other. Another object of the invention is to provide a fan retractor capable of minimizing caving of abdominal tissue into the working space provided by lifting. Still another object is to provide a mechanical retractor with lifting rods which may be placed in spaced relationship without pivotal movement relative to one another so as to reduce the possibility that the lifting rods will catch on abdominal tissue during deployment.

An abdominal wall retractor according to the present invention comprises a pair of lifting rods and an elongate cross-member connected at their ends to form a triangular lifting area. The rods and the member are connected for relative movement therebetween such that the apparatus can be pivoted into a streamlined configuration for insertion into an abdominal cavity through a puncture opening in an abdominal wall and subsequently pivoted to and locked in a triangular lifting position where they are used to raise and support the abdominal wall, thus creating a work space for laparoscopic surgery.

DETAILED DESCRIPTION OF THE INVENTION

The present invention is comprised generally of a pair of lifting rods 10, 12, a pair of lifting members 14, 16 integral with the rods 10 and 12, and a cross-member 18.

Figure 1:
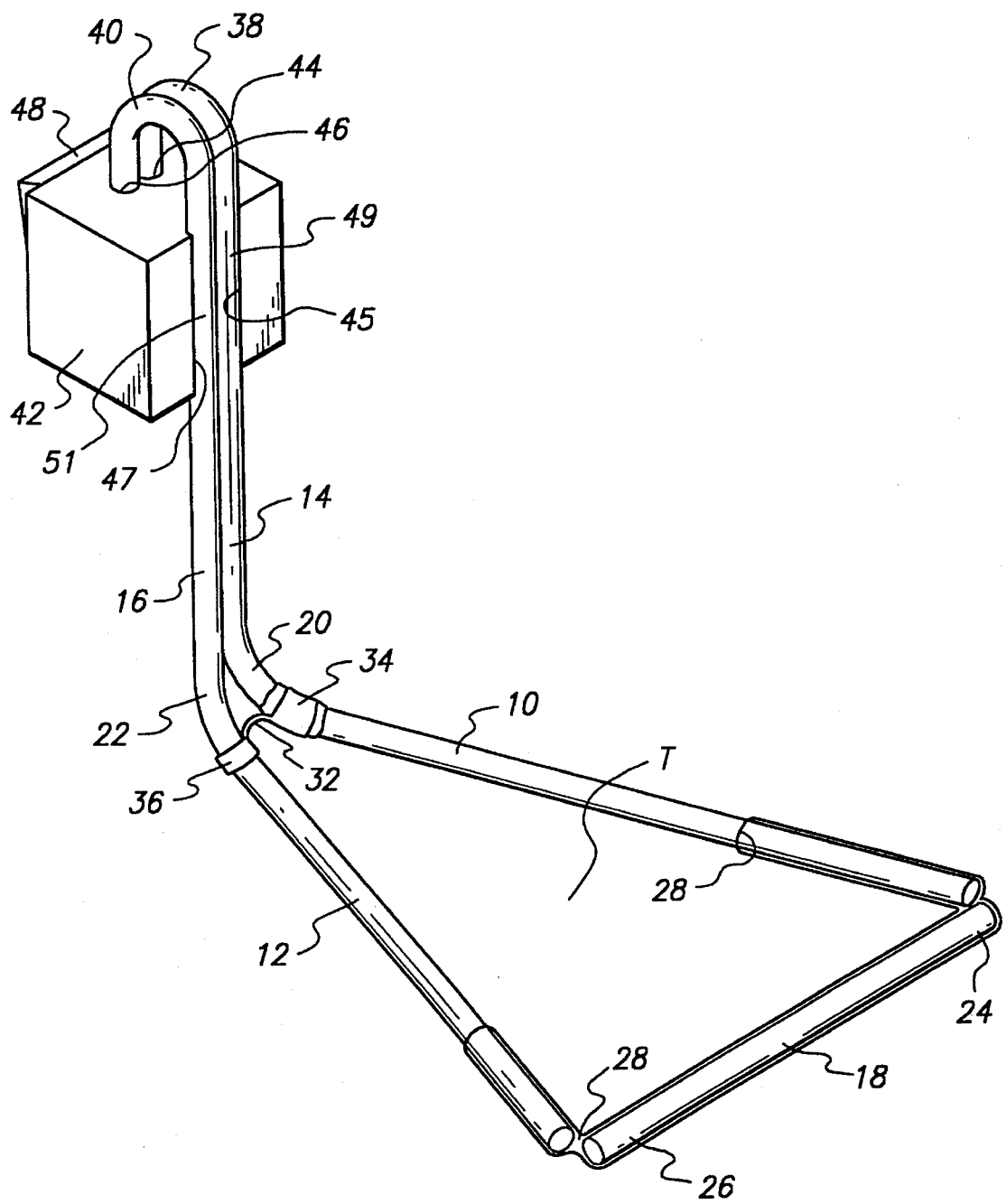
FIG. 1 is a perspective view of a preferred embodiment of a lifting retractor according to the present invention in the triangular lifting position.

Referring to FIG. 1, each lifting rod 10, 12 has a proximal end which forms an elbow 20, 22 with a lifting member 14, 16. The cross-member 18 is an elongate member having two ends 24, 26. The distal ends of the lifting rods 10, 12 and the ends 24, 26 of the cross-member 18 are hinged together by a section of plastic tubing 28 disposed around the respective ends of the lifting rods and cross-member as shown in FIG. 1, such that the lifting rods and cross-members are capable of pivoting around their hinged ends. While tubing made from a plastic, such as an elastomeric or other semi-rigid material, is the preferred hinging means, numerous other hinging means including rivets may be utilized without exceeding the scope of the present invention.

The lifting members 14, 16 preferably have hooks 38, 40 formed at their proximal ends. A mounting block 42 is provided having a pair of bores 44, 46 proportioned for receiving the hooks 38, 40 and a pair of grooves 45, 47 for receiving the proximal portion 49, 51 of the lifting members 14, 16.

Figure 5:
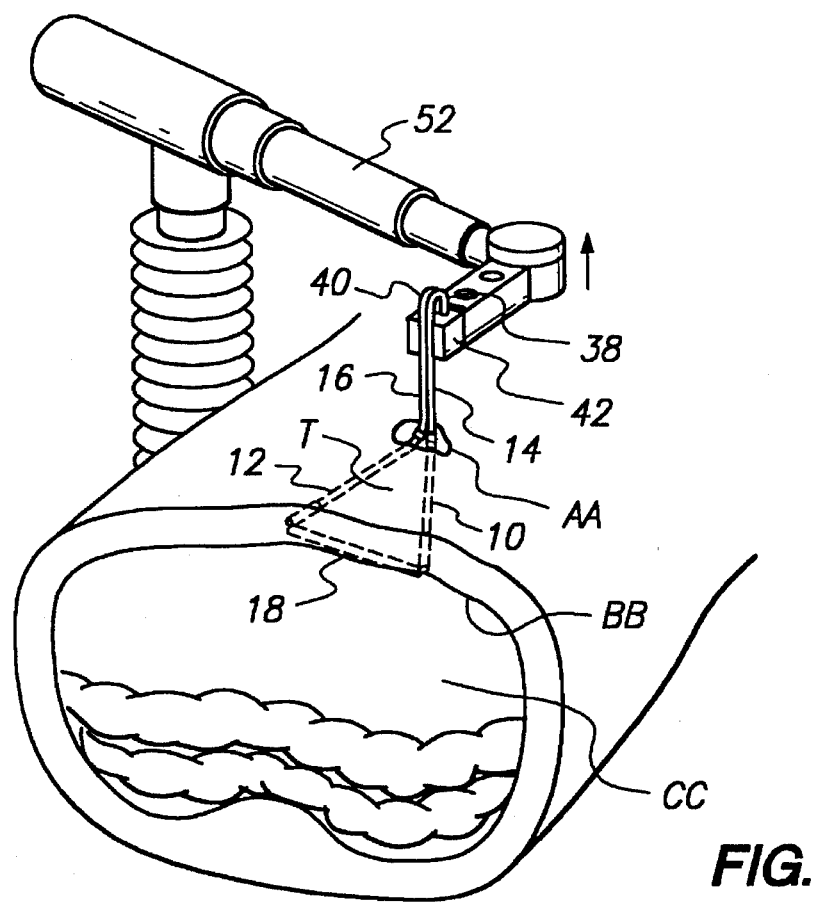
FIG. 5 is a perspective view of the preferred embodiment of FIG. 1 in the lifting position schematically showing the apparatus connected to a mechanical lifting arm and positioned inside an abdominal cavity.
Figure 6:
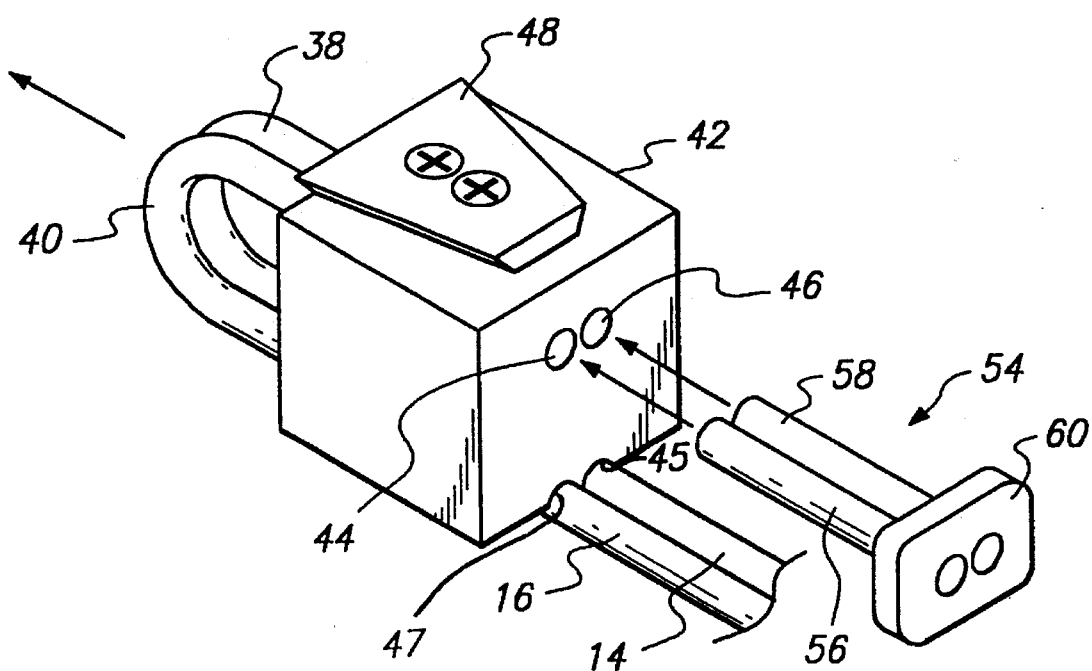
FIG. 6 is a perspective view of a plunger device for dismounting the apparatus of the preferred embodiment from its mounting block.

As shown in FIG. 6, a plunger device 54 is provided for ejecting the hooks 38, 40 from the mounting block 42. The plunger device has a pair of spaced rods 56, 58 secured to a plate 60. The rods 56, 58 are proportioned to be received by the distal ends of the bores 44, 46 in the mounting block 42 such that the portions of hooks 38, 40 positioned in the bores 44, 46 can be ejected out of the bores by inserting rods 56, 58 into the bores and pushing upwards as indicated by arrows. The mounting block 42 is further fitted with a dovetail connector 48 receivable by a dovetail slot (not shown) on a mechanical lifting arm 52 (see FIG. 5).

The elbow 20 between lifting rod 10 and lifting member 14 is tied to lifting rod 12 by a strap 32 or other form of tying means. The strap 32 is secured around the elbow 20 of lifting rod 10 but is disposed around lifting rod 12 in such a way that the lifting rod 12 is slidable from end to end within the strap (see FIGS. 2 and 3). The strap 32 is preferably constructed of two sections 34, 36 of elastomeric tubing bonded together, with one section 34 disposed around the elbow 20 of lifting rod 10 and the other section 36 loosely disposed around lifting rod 12 such that the lifting rod 12 is slidable within section 36 while section 34 remains secured to elbow 20.

Figure 2:
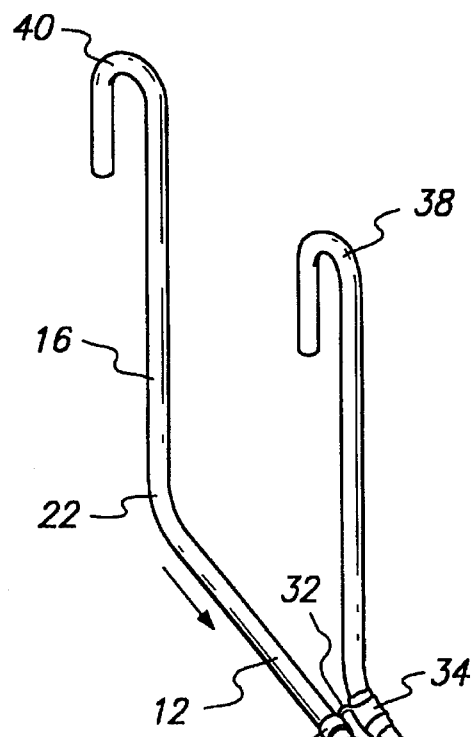
FIG. 2 is a perspective view of the preferred embodiment of FIG. 1 showing the apparatus in the streamlined insertion position.
Figure 3:
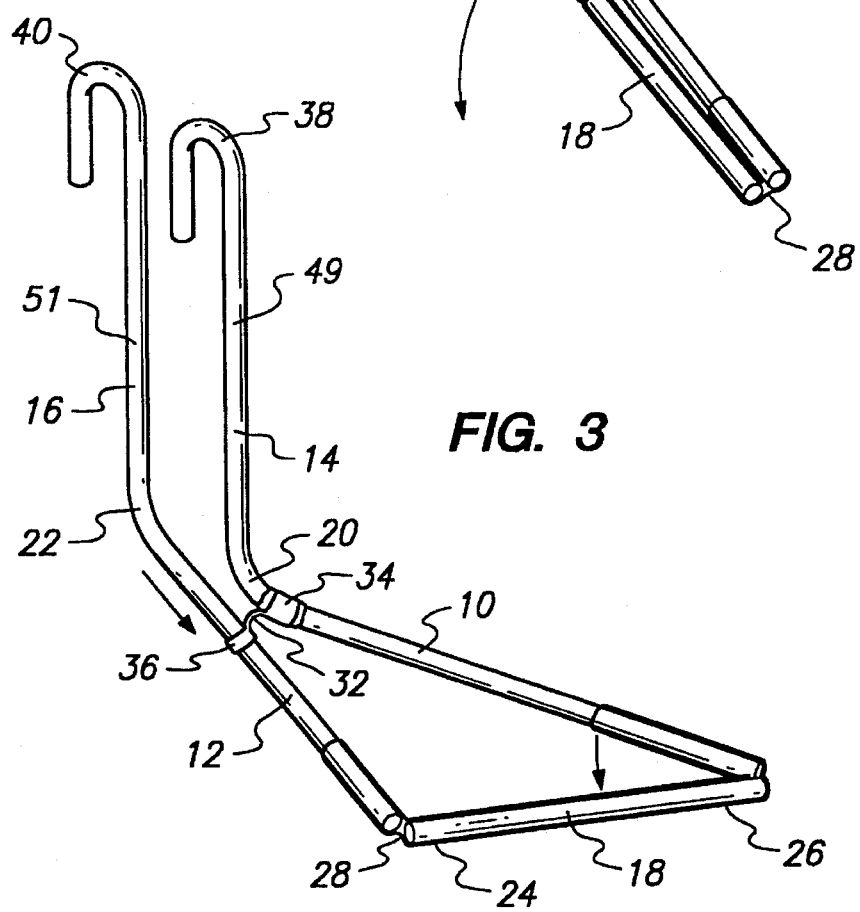
FIG. 3 is a perspective view of the preferred embodiment of FIG. 1 showing the apparatus partially opened into the triangular lifting position.

The hinged connections between the lifting rods 10, 12 and the cross-member 28 and the tying together of the lifting rods by the strap 32 allow the apparatus to be pivoted from a streamlined insertion position shown in FIG. 2 to a lifting position shown in FIG. 1. In the insertion position, the cross-member is pivoted around the distal ends of the lifting rods 10, 12 such that lifting rod 12 and the cross-member are substantially longitudinal of each other and lifting rod 10 is adjacent to lifting rod 12 and the cross-member 18. To move the apparatus from the insertion position to the lifting position, lifting member 16 is advanced in a distal direction such that it slides through the section 36 of elastomeric tubing. Referring to FIG. 3, as the lifting rod 12 advances distally through tubing section 36, end 26 of the cross-member 18 begins to pivot around the distal end of lifting rod 10 and the distal end of lifting rod 12 and end 24 of cross-member 18 begin to pivot relative to each other to form angles between the lifting rods and the cross-member. The lifting member 16 is advanced until the lifting members 14, 16 are side-by-side as shown in FIG. 1 and the lifting rods 10, 12 and the cross-member 18 define the triangular lifting area T.

Figure 7:
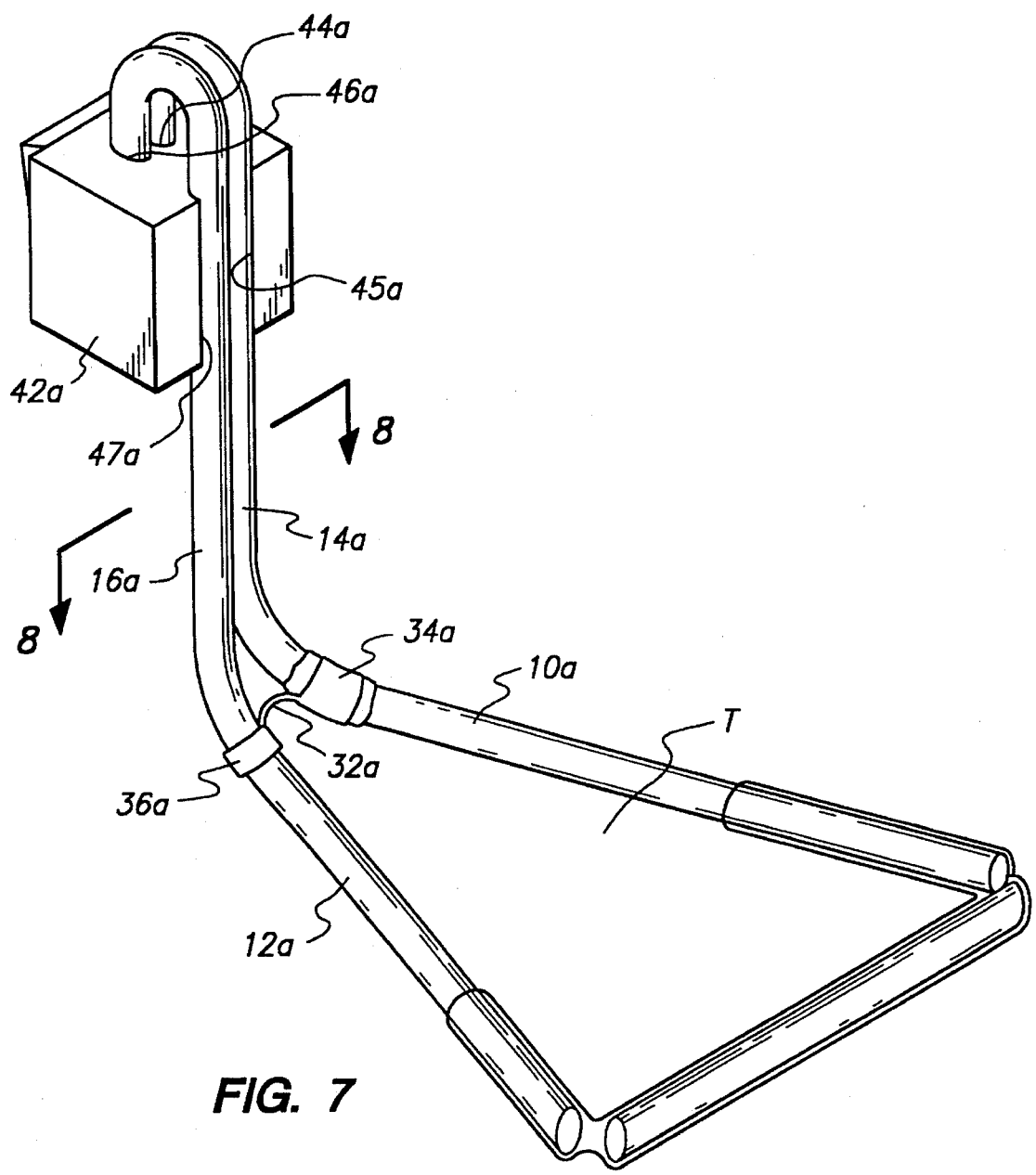
FIG. 7 is a perspective view of a lifting retractor according to the present invention in the triangular lifting position and having lifting rods and lifting members having elliptical cross-sections.
Figure 8:
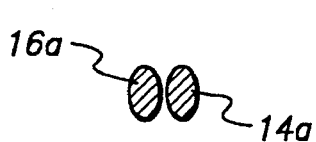
FIG. 8 is a cross-sectional top view of the lifting members of the lifting retractor of FIG. 7.
Figure 9:
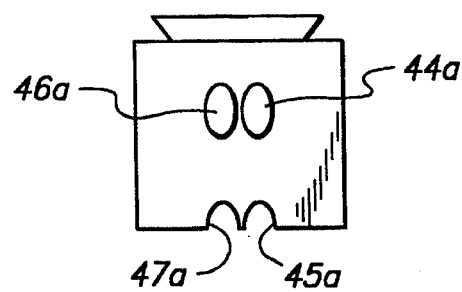
FIG. 9 is a top view of a mounting block of the lifting retractor of FIG. 7.

Rods 10, 12 and lifting members 14, 16 can be made having a circular cross-section or they can be made to have an elliptical or asymmetric cross-section to provide resistance to twisting or rolling along the longitudinal axis which may occur during deployment or upon load. For example, providing rods 10a, 12a having asymmetric or elliptical cross-sections, such as those shown in FIG. 7, and providing similarly shaped sections 34a, 36a on strap 32a will limit rolling or twisting of the rods by keying the rods to the strap. Moreover, if lifting members 14a, 16a are configured to have the elliptical cross-section shown in FIGS. 7 and 8, the lifting members are less able to roll around each other when subjected to inwardly directed lateral forces such as those exerted on the retractor by the abdominal wall. The bores 44a, 46a and grooves 45a, 47a in the mounting block 42a will have a corresponding elliptical shape as shown in FIG. 9 and will thus provide additional resistance against rotation of the lifting members 14a, 16a within the bores 44a, 46a because of the added keying that will occur between the elliptic lifting members 14a, 16a and the corresponding elliptic bores and grooves 45a, 47a.

Figure 4:
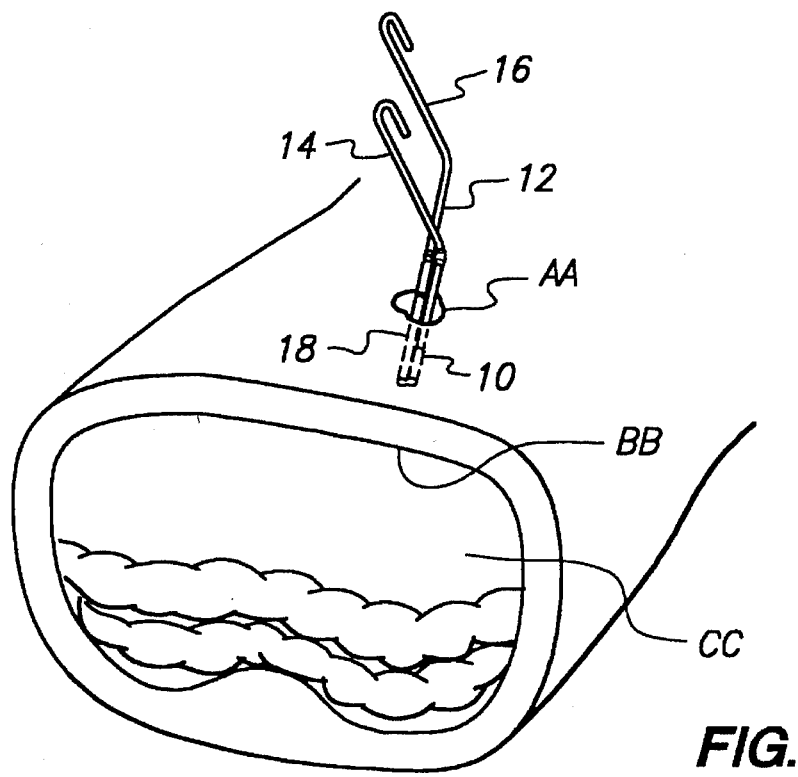
FIG. 4 is a perspective view of the preferred embodiment of FIG. 1 in the insertion position schematically showing insertion of the apparatus into an abdominal cavity through a puncture opening in an abdominal wall.

Clinical use of the apparatus will next be described with reference to FIGS. 4 and 5. A puncture opening AA is first formed in the abdominal wall BB. For insertion of the retraction system through the puncture opening, the apparatus must be placed in the streamlined condition of FIG. 2 with the cross-member 18 pivoted toward lifting rod 10 such that strap 32 is disposed near the distal end of lifting rod 12.

The cross-member 18 and the lifting rod 10 are next inserted through the puncture opening AA and advanced into the abdominal cavity CC such that elbow 20 is positioned at puncture opening AA. Lifting member 16 is next advanced as described above to cause the lifting rod 12 and the cross-member 18 to pivot into the lifting position and to form the triangular lifting area T shown in FIGS. 1 and 5.

The hooks 38, 40 formed at the proximal ends of the lifting rods are next inserted into the bores 44, 46 of mounting block 42 so as to maintain lifting area T. Referring to FIG. 1, when the hooks 38, 40 are positioned in the bores, the proximal portions 49, 51 are disposed within the grooves 45, 47 of the mounting block 42. As shown in FIG. 6, the dovetail connector 48 is then joined to mechanical lifting arm 52 which delivers a lifting force to the apparatus for lifting the abdominal wall. During lifting, the cross-member 18 provides a barrier which helps to prevent abdominal tissue from draping between the lifting rods 10, 12. It also helps the lifting rods 10, 12 resist the inward forces imposed on them by the abdominal wall and thus prevents the rods from moving towards each other during lifting.

Conclusion

The apparatus of the present invention has been described with respect to a single embodiment but is intended to be limited only in terms of the appended claims.

I claim:

1. An apparatus for laparoscopically lifting an abdominal wall, the apparatus comprising:

first and second lifting members, each having a longitudinal axis;

first and second lifting rods each extending angularly from a corresponding one of the first and second lifting members, each lifting rod having a proximal end and a distal end;

a cross-member having two ends, one end hinged to the distal end of the first lifting rod and the other end hinged to the distal end of the second lifting rod;

connecting means for connecting the lifting rods such that the lifting rods are movable between a streamlined condition, in which the lifting members are spaced by a first distance and in which the lifting rods and cross-member are configured for insertion through a small laparoscopic incision in an abdominal wall, and a lifting position in which the lifting members are spaced by a second distance smaller than the first distance and in which the lifting rods and the cross-member form a substantially triangular lifting area for interior engagement of the abdominal wall and in which the lifting rods and cross-member occupy a lifting plane which extends transversely across the longitudinal axes of the lifting members; and lifting means for delivering a lifting force to the lifting rods.

2. The apparatus of claim 1 wherein:

the connecting means comprises tying means for tying the proximal end of the first lifting rod to the second lifting rod such that the second lifting rod is moveable in a linear direction relative to the proximal end of the first lifting rod and such that when in the streamlined condition the cross-member extends substantially longitudinally of the distal end of the second lifting rod; and the apparatus further comprises locking means for locking the lifting rods in the lifting position.

3. The apparatus of claim 2 wherein:

the locking means comprising means for locking the lifting members in side by side relation.

4. The apparatus of claim 3 wherein in the lifting position the proximal end of the second lifting rod is connected to the proximal end of the first lifting rod by the tying means and the lifting members are positioned in side-by-side relation.

5. The apparatus of claim 4 wherein the lifting members have proximal ends and wherein the locking means comprises a locking block having a pair of bores proportioned for receiving the proximal ends of the lifting members when the lifting rods are in the lifting position.

6. The apparatus of claim 1 wherein the tying means connects the proximal ends of the lifting rods for slidable movement of the rods relative to one-another.

7. The apparatus of claim 1 further comprising means for coupling the first and second lifting rods against relative rotational movement about their longitudinal axes.

8. An apparatus for laparoscopically lifting an abdominal wall, the apparatus comprising:

first and second lifting rods each having a proximal end and a distal end;

a pair of lifting members, the first lifting member joined in angular relation to the first lifting rod and the second lifting member joined in angular relation to the second lifting rod, each lifting member having a proximal end, a distal end, and a middle section between the proximal and distal ends;

a cross-member having two ends, one end hinged to the distal end of the first lifting rod and the other end hinged to the distal end of the second lifting rod such that the lifting rods have a streamlined condition, in which the lifting rods and cross-member are configured for insertion of the lifting rods and cross-member into a small laparoscopic incision in an abdominal wall, and a lifting position in which the lifting rods and the cross-member form a substantially triangular lifting area;

tying means for tying the proximal end of the first lifting rod to the second lifting rod such that the second lifting rod is moveable in a linear direction relative to the proximal end of the first lifting rod and such that when in the streamlined position the cross-member extends substantially longitudinally of the distal end of the second lifting rod and when in the lifting position the proximal end of the second lifting rod is connected to the proximal end of the first lifting rod by the tying means and the lifting members are positioned in side-by-side relationship;

lifting means for delivering a lifting force to the lifting rods; and a locking block having a pair of bores proportioned for receiving the proximal ends of the lifting members when the lifting rods are in the lifting position and further having a pair of grooves formed in the locking block for receiving the middle sections of the lifting members.

9. An apparatus for use in laparoscopically lifting an abdominal wall, the apparatus comprising:

a first lifting rod, including a first proximal section and a first distal section extending angularly from the first proximal section;

a second lifting rod including a second proximal section and a second distal section extending angularly from the second proximal section, the first and second distal sections pivotally and slidably connected to each other; and a link hinged between the first and second distal sections such the rods have:

a first condition in which the first and second distal sections are juxtaposed, with the link extending longitudinally thereof, for insertion through a small laparoscopic incision in an abdominal wall, and in which the first and second proximal sections are spaced by a first distance, and a second condition in which the first and second distal sections are in a spread condition with the link extending between them for interiorly engaging an abdominal wall, and in which the first and second proximal sections are spaced by a second distance which is smaller than the first distance, and in which the first and second distal sections occupy a lifting plane which extends transversely across the longitudinal axes of the proximal sections of the lifting rods.

* * * * *